United States Patent
Schneider et al.

(10) Patent No.: US 6,942,772 B1
(45) Date of Patent: Sep. 13, 2005

(54) MEASURING SENSOR FOR THE DETERMINATION OF A CONCENTRATION OF GAS CONSTITUENTS IN GASEOUS MIXTURES

(75) Inventors: Jens Stefan Schneider, Anderson, SC (US); Gerhard Hoetzel, Stuttgart (DE); Bernd Schumann, Rutesheim (DE); Thomas Moser, Schwieberdingen (DE)

(73) Assignee: Robert Bosch GmbH, Stuttgart (DE)

( * ) Notice: Subject to any disclaimer, the term of this patent is extended or adjusted under 35 U.S.C. 154(b) by 414 days.

(21) Appl. No.: 09/786,903

(22) PCT Filed: Jun. 29, 2000

(86) PCT No.: PCT/DE00/02124

§ 371 (c)(1),
(2), (4) Date: May 9, 2001

(87) PCT Pub. No.: WO01/04616

PCT Pub. Date: Jan. 18, 2001

(30) Foreign Application Priority Data

Jul. 9, 1999 (DE) ................................ 199 32 048

(51) Int. Cl.$^7$ ......................................... G01N 27/409
(52) U.S. Cl. ...................................... 204/424; 204/426
(58) Field of Search ................................ 204/421–429

(56) References Cited

U.S. PATENT DOCUMENTS

| 3,843,400 | A | * | 10/1974 | Radford at al. |
| 4,487,680 | A | * | 12/1984 | Logothetis et al. |
| 4,720,335 | A | * | 1/1988 | Fukushima et al. |
| 5,630,920 | A | * | 5/1997 | Friese et al. |
| 5,897,759 | A | * | 4/1999 | Kurosawa et al. |
| 6,019,881 | A | * | 2/2000 | Kurosawa et al. |
| 6,143,165 | A | * | 11/2000 | Kurosawa et al. |
| 6,168,700 | B1 | * | 1/2001 | Kohler et al. |
| 6,218,036 | B1 | * | 4/2001 | Shiratori |

FOREIGN PATENT DOCUMENTS

| DE | 44 08 361 | 9/1995 |
| DE | 44 08 504 | 9/1995 |

OTHER PUBLICATIONS

Merriam- Webster's Collegiate Dictionary, 10th ed., (1998), p. 187.*

* cited by examiner

Primary Examiner—Kaj K. Olsen
(74) Attorney, Agent, or Firm—Kenyon & Kenyon

(57) ABSTRACT

A sensor for determining a concentration of gas components in gas mixtures having a first measuring electrode (mixed potential electrode) which has little or no catalytic effect on the establishment of an equilibrium in the gas mixture and a second measuring electrode (equilibrium electrode) which catalyzes the establishment of an equilibrium in the gas mixture as well as a solid electrolyte that is conductive for oxygen ions arranged between the two measuring electrodes, with the two measuring electrodes being exposed to the gas mixture. At least the first measuring electrode (16) is a cermet electrode, where at least one metal oxide component of the cermet electrode is capable of reversible incorporation of oxygen.

26 Claims, 1 Drawing Sheet

MEASURING SENSOR FOR THE DETERMINATION OF A CONCENTRATION OF GAS CONSTITUENTS IN GASEOUS MIXTURES

BACKGROUND INFORMATION

Sensors for determining the concentration of gas components in gas mixtures, in particular in gases from internal combustion engines, are known. Such sensors are used to preset a fuel/air mixture for operation of the internal combustion engine on the basis of a determination of the oxygen concentration and/or the concentration of reducing gas components such as HC or CO. A specific operating state can be characterized by using the ratio of the oxygen concentration to the fuel concentration. If there is a stoichiometric excess of fuel (rich range), the amount of oxygen in the exhaust gas will be small in comparison with other components, which are partially uncombusted. In the lean range, where oxygen from air is predominant in the fuel/air mixture, the oxygen concentration in the exhaust gas is accordingly high.

To determine the oxygen concentration in the exhaust gas, there are known lambda sensors which detect a lambda value>1 in a lean range, a lambda value<1 in the rich range and a lambda value=1 in a stoichiometric range. In a known manner, an electrochemical measuring cell of the sensor supplies a detection voltage which is sent to a circuit arrangement. The detection voltage depends on an oxygen concentration difference at the at least two measuring electrodes used. A solid electrolyte body which is conductive for oxygen ions is arranged between the measuring electrodes. The detection voltage increases or decreases according to the oxygen concentration in the exhaust gas.

In addition, there are known sensors which are used to determine the concentration of the reducing gas components.

These sensors are often component specific, i.e., there is a separate sensor for each gas component ($H_2$, HC and CO) to be detected.

Both types of sensor supply either a value for the oxygen concentration or the concentration of the reducing gas components. Thus, they supply values which give only an indirect indication of the status of the lambda value. Thus, a sensor for determining oxygen concentrations can supply a certain absolute oxygen concentration from which it is possible to infer the composition of the fuel/air mixture.

A more precise setting of a control status of an internal combustion engine can be achieved by determining the lambda value directly. It is advantageous here to have a compact sensor capable of handling both sensor functions instead of two separate sensors, one for each gas component. Previous attempts to accommodate multiple sensor functions on one substrate have resulted in a complicated layout or a complicated layer structure which has a greater susceptibility to faults and entails high manufacturing costs.

The reducing gas components in the exhaust gas of internal combustion engines are in a thermodynamic equilibrium with the oxygen. The further away the sensors are arranged from the engine in an exhaust duct of the internal combustion engine, the lower the temperature of the exhaust gas, and thus it is difficult to establish a thermodynamic equilibrium from a kinetic standpoint. It is known that the equilibrium reaction can be catalyzed with transition metals. In particular, catalysts containing platinum, palladium or rhodium have proven suitable. In using these metals as the electrode material for the measuring electrodes of sensors, it has proven especially advantageous to have such a catalytic activity on a measuring electrode which is exposed to the exhaust gas. In this way, the oxygen concentration at this measuring electrode can be kept very low, thus yielding a very high potential difference with respect to another electrode exposed to a reference gas. However, such a measuring electrode which catalyzes the establishment of an equilibrium in the gas mixture (equilibrium electrode) does not permit detection of the concentration of the reducing gas components.

Therefore, it is known that materials which inhibit a catalytic effect of the measuring electrode can be added to the measuring electrode exposed to the gas mixture. Thus, German Patent No. 44 08 361 describes a measuring electrode in which adsorption of oxygen on a surface of the measuring electrode has been made possible by the addition of bismuth, platinum, antimony or lead. Thus, the oxygen concentration, which determines the potential of the measuring electrode, at a ternary boundary of the measuring electrode is kept almost constant in operation of the internal combustion engine at lambda>1. The measuring electrode designed in this way reacts essentially to oxygen and is thus a non-equilibrium electrode or a mixed potential electrode. Such a measuring electrode can thus be used as a reference electrode at lambda>1.

In addition, it is known from German Patent No. 44 08 504 that such a mixed potential electrode can be designed by admixture of gold and/or silver. Due to the admixture of gold and/or silver, the catalytic conversion is inhibited by oxidation of CO and/or HC and reduction of $NO_x$. The high affinity of these metals for the reducing gas components is utilized at the measuring electrode. The oxygen concentration and thus the potential of the mixed potential electrode can be kept almost constant due to adsorption of the reducing gas components at the surface of the mixed potential electrode in operation of the internal combustion engine at lambda<1. In this way, such a measuring electrode can be used as a reference electrode at lambda<1. One disadvantage of these two described embodiments of mixed potential electrodes is that they permit only constant potentials for two extreme positions of the lambda value and thus omit the range at lambda values= 1, which is especially interesting for control of the control status of the internal combustion engine. In addition, it is impossible in this way to determine the oxygen concentration on the one hand or the concentration of reducing gas components on the other hand by using one and the same measuring electrode.

SUMMARY OF THE INVENTION

It is possible to determine either the oxygen concentration or the concentration of a reducing gas component with an arrangement of just two measuring electrodes by using the sensor according to the present invention for determining a concentration of gas components in gas mixtures having a first measuring electrode (mixed potential electrode) which has little or no catalytic effect on the establishment of an equilibrium in the gas mixture and a second measuring electrode (equilibrium electrode) which catalyzes the establishment of an equilibrium in the gas mixture as well as a solid electrolyte that is conductive for oxygen ions arranged between the two measuring electrodes, with the two measuring electrodes being exposed to the gas mixture. Due to the fact that at least the first measuring electrode is a cermet electrode, where at least one metal oxide component of the cermet electrode is capable of reversible incorporation of oxygen, the potential of this first measuring electrode is kept almost constant in the range around lambda≈1. Thus, the first measuring electrode is the reference electrode in this operating state of the internal combustion engine, while the second measuring electrode functions as the working electrode. If the operating state of the internal combustion engine changes to a range with lambda>1, then the potential of the second measuring electrode is almost constant, while the potential of the first measuring electrode is variable and is determined essentially by the concentration of the reducing gas components. Thus in this case the second measuring electrode is the reference electrode and the first measuring electrode is the working electrode.

Suitable metal oxide components for the first measuring electrode include, for example, the mixed oxides such as $TiNiNbO_x$ or $FeNiMnO_4$. Furthermore, a noble metal such as gold may also be incorporated into the first measuring electrode. It is thus possible to adapt the potential of the first measuring electrode very accurately to the requirements of a given application.

In a preferred embodiment of the present invention, a reference electrode additionally exposed to a reference gas is provided for the two measuring electrodes exposed to the gas mixture. The measuring electrodes may be arranged side by side, i.e., both in the same layer of a multilayer sensor. However, it is also conceivable for the two measuring electrodes to be arranged one after the other in different layers, starting from an outer side of the sensor in the direction of the reference electrode. One layer between the two measuring electrodes must be sufficiently porous so that it allows a sufficiently rapid establishment of an equilibrium in the constantly changing concentrations of the individual exhaust gas components. One measuring electrode corresponds to the mixed potential electrode based on oxygen-storing metal oxide components and the other measuring electrode is designed as an equilibrium electrode.

It has proven advantageous to arrange the mixed potential electrode closer to the exhaust gas because it has an especially stable and constant potential in rapid gas changes at lambda values around 1. In addition to an equilibrium electrode which naturally has a catalytic activity, it is also conceivable to incorporate additional catalysts or promoters into the porous intermediate layer, although of course not in the immediate vicinity of the mixed potential electrode. In this way, it is possible to have a controlled influence on the establishment of an equilibrium in the mixture, thus yielding the possibility of using other metal components that are not catalytically active for the equilibrium electrode.

With the help of this preferred arrangement with a total of only three electrodes, the oxygen concentration and the concentration of the reducing gas components can be determined simultaneously in certain operating states and thus the status of the lambda value can be determined directly. This permits a much more rapid and accurate establishment of the control status of the internal combustion engine. In addition, such a sensor can be implemented in an especially simple and inexpensive manner.

DETAILED DESCRIPTION

Figure 1:
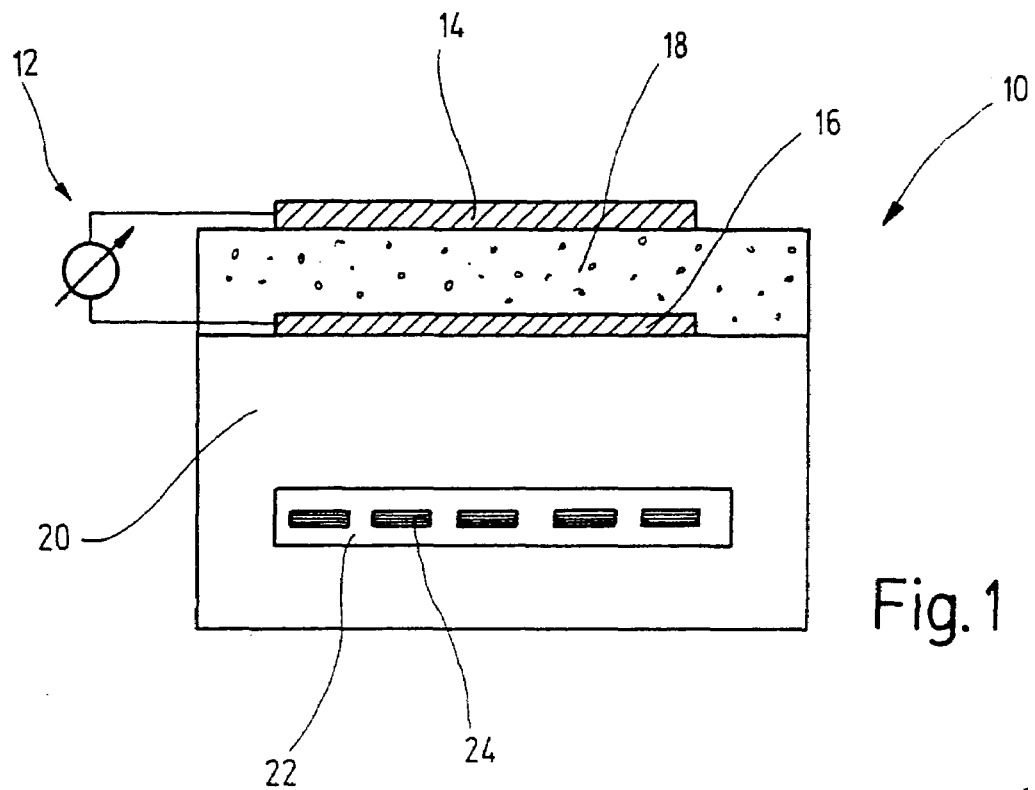
FIG. 1 shows a schematic sectional view through a sensor.

FIG. 1 shows a sensor 10 which can be used for determination of the concentration of gas components in gas mixtures, in particular the exhaust gases of internal combustion engines. Such a sensor 10 is preferably composed of individual ceramic layers which may be structured in a known way by screen printing, lamination, cutting, sintering or the like. Sensor 10 contains an electrochemical measuring cell 12 having a first measuring electrode 14 and a second measuring electrode 16, with a porous oxygen ion conducting layer 18 extending between two measuring electrodes 14, 16. A heating element 22 is arranged beneath second measuring electrode 16 in a layer 20 which at least conducts heat well. Heating element 22 includes a resistance element 24, designed as a meandering element here, and it functions to establish or control an operating temperature of sensor 10. Second measuring electrode 16 is composed of a noble metal cermet, e.g., based on a noble metal such as platinum. This second measuring electrode 16 is referred to below as equilibrium electrode 16 because of the catalytic activity of these noble metals with regard to the equilibrium reaction between oxygen and reducing gas components of the exhaust gas as explained below. As also to be explained below, first measuring electrode 14 has little or no catalytic activity in certain operating states of the internal combustion engine, which can be characterized by a lambda value, and it is referred to below as mixed potential electrode 14.

During combustion of a fuel/air mixture in the internal combustion engine, reducing gas components which can react with the oxygen and are thus in a thermodynamic equilibrium with it are formed in variable amounts. In addition to a temperature-dependent equilibrium status of this reaction, the kinetics of the reaction is especially important for establishing the equilibrium. It may essentially be assumed that the temperature of the exhaust gas drops with an increase in the distance of sensor 10 from the engine, and thus it becomes more difficult for a thermodynamic equilibrium to be established from a kinetic standpoint. Due to the noble metals such as platinum, palladium and rhodium used in equilibrium electrode 16, establishment of this equilibrium is catalyzed. Thus, the potential of equilibrium electrode 16 is determined essentially by the oxygen concentration.

The potential of mixed potential electrode 14, however, does not depend on the oxygen concentration, at least in some ranges, but instead it is a function of the concentration of reducing gas components. It is thus possible to influence the potential of mixed potential electrode 14 in a controlled manner by selecting at least one metal oxide component capable of reversible incorporation of oxygen. Such a mixed potential electrode 14 may be made mostly of $TiNiNbO_x$ or $FeNiMnO_4$. It is also conceivable to use metal oxides such as $Mn_2O_3$ and $CeO_2$. In addition, the cermet electrode may also contain as an added metal component a noble metal such as gold or silver. In this way, the potential of mixed potential electrode 14 can be adapted individually to the requirements of given applications.

In an operating mode of internal combustion engine where $\lambda \approx 1$, the oxygen concentration directly at a surface of mixed potential electrode 14 is kept almost constant due to the added metal oxide components. A capacity for incorporation and disincorporation of oxygen in a mixed potential electrode 14 determines a lambda range in which the potential of mixed potential electrode 14 is almost constant. However, the potential on equilibrium electrode 16 in such an operating mode of the internal combustion engine is exposed to great variations, because there are great variations in oxygen concentration precisely in such a lambda range. Thus at $\lambda \approx 1$, mixed potential electrode 14 can be used as a reference electrode, while equilibrium electrode 16 can be used as a working electrode 16. Then a detection voltage U which is a direct measure of the oxygen concentration of the gas mixture can be picked off via electrochemical measuring cell 12. When the operating mode of the internal combustion engine changes to a range of $\lambda>1$, then the potential of mixed potential electrode 14 changes greatly with a change in the concentration of the reducing gas components. However, the potential of equilibrium electrode 16 is almost constant at high oxygen concentrations. Thus in this case, equilibrium electrode 16 functions as the reference electrode and mixed potential electrode 14 functions as the working electrode. Then a detection voltage U corresponding to the concentration of the reducing gas components can be picked off via electrochemical measuring cell 12.

In principle, an arrangement of two measuring electrodes 14, 16 may be in the opposite order from that shown here, but in the case of the arrangement shown here, additional promoters or catalysts that support the establishment of an equilibrium may be incorporated into layer 18. In this way it is possible to vary the composition of equilibrium electrode 16 to a great extent, and it is not necessary to use such relatively expensive noble metals as platinum or palladium.

Figure 2:
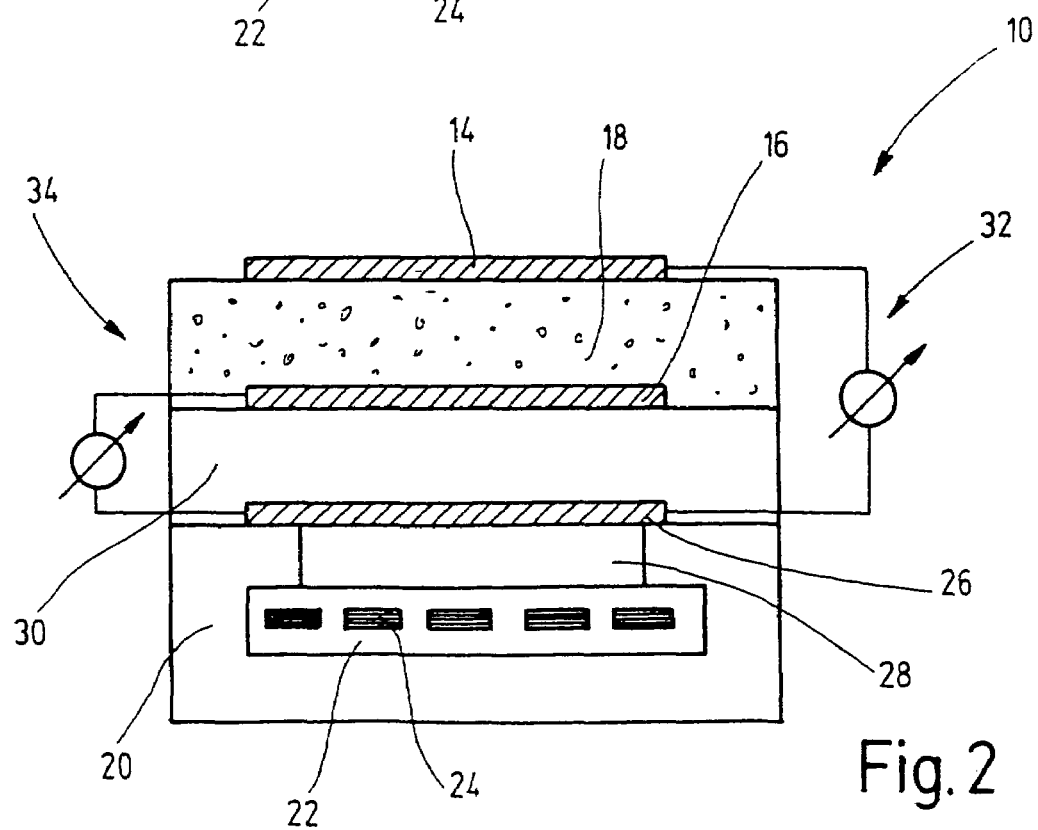
FIG. 2 shows a schematic sectional view through another embodiment of a sensor.

FIG. 2 shows a preferred additional embodiment of sensor 10. In addition to two measuring electrodes 14, 16 described above, sensor 10 has another reference electrode 26. Reference electrode 26 is above a reference channel 28 which is filled with a reference gas. Heating device 22 is used first for heating sensor 10 and also for heating the reference gas. Between reference electrode 26 and equilibrium electrode 16 there is a layer 30 composed of a solid electrolyte that is conductive for oxygen ions. Such a sensor 10 has a first electrochemical measuring cell 32, which includes mixed potential electrode 14 and reference electrode 26, and a second electrochemical measuring cell 34, which includes equilibrium electrode 16 and reference electrode 26.

With the help of this very simple arrangement with only three electrodes, the oxygen concentration and the concentration of the reducing gas components can be measured simultaneously as a function of the operating mode of the internal combustion engine. In this way, a lambda value can be determined very rapidly and with high precision.

Thus, for example, at a lambda value>1, the potential of mixed potential electrode 14 depends essentially on the concentration of the reducing gas components, as mentioned above, and thus it can be picked off as a detection voltage $U_1$ via electrochemical measuring cell 32. In the same operating mode, a potential difference between equilibrium electrode 16 and reference electrode 26 can also be detected if the reference gas has a sufficiently different oxygen concentration. The potential difference then leads to a detection voltage $U_2$ which can be picked off at electrochemical measuring cell 34 and is a direct measure of the oxygen concentration.

In addition to the arrangement shown here, where measuring electrodes 14, 16 are arranged in successive layers of sensor 10, an arrangement in one and the same layer is also conceivable. In this way, sensor 10 is also simpler to manufacture, i.e., fewer steps are involved.

What is claimed is:

1. A sensor for determining a concentration of gas components in a gas mixture, comprising:
   a first measuring electrode having substantially no catalytic effect on an establishment of an equilibrium in the gas mixture when exposed to the gas mixture, the first measuring electrode including a cermet electrode with at least one metal oxide component, the at least one metal oxide component being capable of reversible incorporation of oxygen;
   a second measuring electrode catalyzing an establishment of an equilibrium in the gas mixture when exposed to the gas mixture;
   a solid electrolyte that is conductive for oxygen ions situated between the first and second measuring electrodes; and
   a porous layer, the solid electrolyte being integrated into the porous layer;
   wherein the cermet electrode includes a metallic component, and
   wherein the sensor is able to determine a concentration of an oxidizable component in the gas mixture.

2. The sensor according to claim 1, wherein the first measuring electrode is substantially composed of mixed oxides with a composition of one of TiNiNbOx and FeNiMnO4.

3. The sensor according to claim 1, wherein the metal oxide component is at least one of CeO2 and Mn2O3.

4. The sensor according to claim 1, wherein the first measuring electrode is a mixed potential electrode and the metallic component is at least one of gold and silver.

5. The sensor according to claim 1, wherein the porous layer contains at least one of promoters and catalysts at least in some areas.

6. The sensor according to claim 1, wherein a potential of lambda=1 is applied when a lambda value of <1 is present in the gas mixture, the potential is applied at the first measuring electrode.

7. The sensor according to claim 1, wherein the metal oxide component is at least one of CeO2 and Mn2O3, and the first measuring electrode is a mixed potential electrode and the metallic component is at least one of gold and silver.

8. The sensor according to claim 7, further comprising:
   a reference electrode exposed to a reference gas; and
   at least one layer composed of an oxygen conducting solid electrolyte situated between the reference electrode and the measuring electrodes.

9. The sensor according to claim 7, further comprising the porous layer extending between the first and second measuring electrodes, one of the first and second measuring electrodes being situated on a side of the sensor facing the gas mixture, another of the measuring electrodes being situated between a reference electrode and the one of the measuring electrodes facing the gas mixture.

10. The sensor according to claim 1, wherein the porous layer contains at least one of promoters and catalysts at least in some areas.

11. A sensor for determining a concentration of gas components in a gas mixture, comprising:
   a first measuring electrode having substantially no catalytic effect on an establishment of an equilibrium in the gas mixture when exposed to the gas mixture, the first measuring electrode including a cermet electrode with at least one metal oxide component, the at least one metal oxide component being capable of reversible incorporation of oxygen;
   a second measuring electrode catalyzing an establishment of an equilibrium in the gas mixture when exposed to the gas mixture;
   a solid electrolyte that is conductive for oxygen ions situated between the first and second measuring electrodes;
   a reference electrode exposed to a reference gas; and at least one layer composed of an oxygen conducting solid electrolyte situated between the reference electrode and the measuring electrodes;

wherein the cermet electrode includes a metallic component, and wherein the sensor is able to determine a concentration of an oxidizable component in the gas mixture.

12. The sensor according to claim 11, wherein the first measuring electrode is substantially composed of mixed oxides with a composition of one of TiNiNbOx and FeNiMnO4.

13. The sensor according to claim 11, wherein the metal oxide component is at least one of CeO2 and Mn2O3.

14. The sensor according to claim 11, wherein the first measuring electrode is a mixed potential electrode and the metallic component is at least one of gold and silver.

15. The sensor according to claim 11, wherein a potential of lambda=1 is applied when a lambda value of <1 is present in the gas mixture, the potential is applied at the first measuring electrode.

16. The sensor according to claim 11, wherein the metal oxide component is at least one of CeO2 and Mn2O3, and the first measuring electrode is a mixed potential electrode and the metallic component is at least one of gold and silver.

17. The sensor according to claim 16, further comprising a porous layer, the solid electrolyte being integrated into the porous layer, wherein the porous layer contains at least one of promoters and catalysts at least in some areas.

18. The sensor according to claim 11, further comprising a porous layer extending between the first and second measuring electrodes, one of the first and second measuring electrodes being situated on a side of the sensor facing the gas mixture, another of the measuring electrodes being situated between a reference electrode and the one of the measuring electrodes facing the gas mixture, the solid electrolyte being integrated into the porous layer.

19. A sensor for determining a concentration of gas components in a gas mixture, comprising:

a first measuring electrode having substantially no catalytic effect on an establishment of an equilibrium in the gas mixture when exposed to the gas mixture, the first measuring electrode including a cermet electrode with at least one metal oxide component, the at least one metal oxide component being capable of reversible incorporation of oxygen;

a second measuring electrode catalyzing an establishment of an equilibrium in the gas mixture when exposed to the gas mixture;

a solid electrolyte that is conductive for oxygen ions situated between the first and second measuring electrodes; and a porous layer extending between the first and second measuring electrodes, one of the first and second measuring electrodes being situated on a side of the sensor facing the gas mixture, another of the measuring electrodes being situated between a reference electrode and the one of the measuring electrodes facing the gas mixture, the solid electrolyte being integrated into the porous layer;

wherein the cermet electrode includes a metallic component, and wherein the sensor is able to determine a concentration of an oxidizable component in the gas mixture.

20. The sensor according to claim 19, wherein the first measuring electrode is substantially composed of mixed oxides with a composition of one of TiNiNbOx and FeNiMnO4.

21. The sensor according to claim 19, wherein the metal oxide component is at least one of CeO2 and Mn2O3.

22. The sensor according to claim 19, wherein the first measuring electrode is a mixed potential electrode and the metallic component is at least one of gold and silver.

23. The sensor according to claim 22, wherein the one of the measuring electrodes facing the gas mixture is the first measuring electrode.

24. The sensor according to claim 19, wherein a potential of lambda=1 is applied when a lambda value of <1 is present in the gas mixture, the potential is applied at the first measuring electrode.

25. The sensor according to claim 19, wherein the metal oxide component is at least one of CeO2 and Mn2O3, and the first measuring electrode is a mixed potential electrode and the metallic component that is at least one of gold and silver.

26. The sensor according to claim 25, wherein the porous layer contains at least one of promoters and catalysts at least in some areas.

* * * * *

UNITED STATES PATENT AND TRADEMARK OFFICE
CERTIFICATE OF CORRECTION

PATENT NO. : 6,942,772 B1
APPLICATION NO. : 09/786903
DATED : September 13, 2005
INVENTOR(S) : Jens Stefan Schneider et al.

It is certified that error appears in the above-identified patent and that said Letters Patent is hereby corrected as shown below:

Column 6, line 18, change "TiNiNbOx" to --TiNiNbO$_x$--

Column 6, lines 18-19, change "FeNiMnO4" to --FeNiMnO$_4$--

Column 6, line 21, change "CeO2 and Mn2O3." to --CeO$_2$ and Mn$_2$O$_3$.--

Column 6, line 30, change "the potential is applied" to --the potential being applied--

Column 6, line 33, change "CeO2 and Mn2O3," to --CeO$_2$ and Mn$_2$O$_3$,--

Signed and Sealed this

Twenty-ninth Day of April, 2008

JON W. DUDAS
*Director of the United States Patent and Trademark Office*